(12) United States Patent
Carliss et al.

(10) Patent No.: US 12,358,868 B2
(45) Date of Patent: Jul. 15, 2025

(54) CHEMICAL DERIVATIVES AND METHODS FOR SYNTHESIZING AND COMPOUNDING CHEMICAL DERIVATIVES RELATED TO CAPSAICIN PALMITATE AND CAPSAICIN PRODRUGS

(71) Applicant: Chorda Pharma, Inc., Roanoke, VA (US)

(72) Inventors: Richard Daniel Carliss, Roanoke, VA (US); Jianxing William Huang, Betlehem, PA (US)

(73) Assignee: Chorda Pharma, Inc., Roanoke, VA (US)

( * ) Notice: Subject to any disclaimer, the term of this patent is extended or adjusted under 35 U.S.C. 154(b) by 41 days.

(21) Appl. No.: 18/454,685

(22) Filed: Aug. 23, 2023

(65) Prior Publication Data

US 2023/0406816 A1    Dec. 21, 2023

Related U.S. Application Data

(60) Division of application No. 17/673,381, filed on Feb. 16, 2022, now Pat. No. 11,773,055, which is a (Continued)

(51) Int. Cl.
C07C 271/40        (2006.01)
C07C 233/22        (2006.01)
(Continued)

(52) U.S. Cl.
CPC .......... C07C 271/40 (2013.01); C07C 233/22 (2013.01); C07C 271/06 (2013.01); C07D 295/205 (2013.01); C07D 295/215 (2013.01)

(58) Field of Classification Search
None
See application file for complete search history.

(56) References Cited

U.S. PATENT DOCUMENTS

2004/0146590 A1    7/2004    Iadarola et al.
2010/0120912 A1    5/2010    Singh et al.
(Continued)

FOREIGN PATENT DOCUMENTS

CN    101774938    *  7/2010
CN    104447777    *  3/2015

OTHER PUBLICATIONS

'Hydrocarbons' ( IUPAC Compendium of Chemical Terminology, 3rd ed. International Union of Pure and Applied Chemistry; 2006. Online version 3.0.1, 2019. https://doi.org/10.1351/goldbook.H02889 ) (Year: 2006).*

(Continued)

*Primary Examiner* — Amy C Bonaparte
(74) *Attorney, Agent, or Firm* — Seed IP Law Group LLP

(57) ABSTRACT

Capsaicin compositions and methods for enhancing hydrophobicity of a molecule useful for pharmaceutical applications, including: (1) a prodrug using a linker such as a carbamate between capsaicin with other structures in order to optimize kinetic control of capsaicin cleavage; (2) a prodrug using a linker such as an unsaturated carboxylic ester between capsaicin with other structures in order to optimize kinetic control of capsaicin cleavage; (3) esters of long-chain fatty acids and capsaicin where hydroxyl groups provide handles for attachment of additional capsaicin molecules; and (4) the use of carboxylic acid diesters to increase overall hydrophobicity of two or more covalently-linked capsaicin molecules. Formulations of palmitated esters of capsaicin are also described, which are designed to enhance hydrophobicity of a molecule useful for pharmaceutical applications, for example to provide compounded mixtures designed to optimize analgesic efficacy.

15 Claims, 2 Drawing Sheets

Related U.S. Application Data continuation of application No. PCT/US2020/046861, filed on Aug. 18, 2020.

(60) Provisional application No. 62/889,002, filed on Aug. 19, 2019.

(51) Int. Cl.
*C07C 271/06* (2006.01)
*C07D 295/205* (2006.01)
*C07D 295/215* (2006.01)

(56) References Cited

U.S. PATENT DOCUMENTS

| 2016/0145225 A1* | 5/2016 | Husfeld | A61P 29/00 |
| | | | 514/330 |
| 2018/0016202 A1* | 1/2018 | Lombardi | C07D 307/33 |
| 2019/0055272 A1 | 2/2019 | Husfeld et al. | |
| 2022/0168259 A1* | 6/2022 | Carliss | A61K 47/542 |

OTHER PUBLICATIONS

Machine generated translation of CN104447777, obtained Nov. 2024 (Year: 2024).*
Machine generated translation of CN 101774938, obtained Nov. 2024 (Year: 2024).*
International Search Report and Written Opinion for Application No. PCT/US2020/046861, dated Dec. 18, 2020, 9 pages.

* cited by examiner

CHEMICAL DERIVATIVES AND METHODS FOR SYNTHESIZING AND COMPOUNDING CHEMICAL DERIVATIVES RELATED TO CAPSAICIN PALMITATE AND CAPSAICIN PRODRUGS

CROSS-REFERENCE TO RELATED PATENT APPLICATIONS

This application is a Divisional application of U.S. Non-Provisional application Ser. No. 17/673,381, filed Feb. 16, 2022, which is a continuation application, filed under 35 U.S.C. § 111(a), based on International Patent Application No. PCT/US2020/046861, filed on Aug. 18, 2020, which claims the benefit of U.S. Provisional Patent Application No. 62/889,002 filed Aug. 19, 2019, the disclosure(s) of each of which are incorporated herein by reference.

BACKGROUND

Technical Field

The present invention relates to capsaicin compositions and methods for enhancing hydrophobicity of a molecule useful for pharmaceutical applications, for example to provide compounded mixtures designed to optimize analgesic efficacy.

Background Art

Capsaicin is the pungent substance in hot chili peppers that causes chemical burning dermal irritation in any tissue of the body in which it contacts. Paradoxically however, capsaicin can produce analgesia when applied as a topical medication. The present invention provides structural modifications of capsaicin or the capsaicinoids (read capsaicin) that modify the cleavage kinetics of the capsaicin prodrug molecule in order to modify the time course of the capsaicin receptor binding process.

A large body of literature demonstrates that capsaicin can produce excellent analgesia. However due to burning, topical capsaicin products currently available for the treatment of pain are dose-limited due to dermal irritation and burning, thereby resulting in poor-to-moderate efficacy and low patient compliance.

Capsaicinoids (including capsaicin), and their close analogs capsinoids, are comprised of a relatively polar vanillyl head group, a long hydrophobic tail, and an amide or ester linkage for capsaicinoids and capsinoids respectively. While all three components (the head group, the hydrophobic tail, and the linkage) have been identified for the associated biological and pharmacological activities, chemical synthesis of analogs of both families have been extensively carried out on the head group and/or the hydrophobic tail. (For some of the recent examples, see: Moriello, A. S. et al. *J. Med. Chem.*, Just Accepted Manuscript, Publication Date (Web): 3 Sep. 2018; Serafini, M. et al. *J. Med. Chem.,* 2018, 61, 4436-4455; Ramsaywack, S. et al. Canadian Journal of Chemistry, Manuscript ID: cjc-2018-0193.R1, date submitted: 2 Jul. 2018; Aiello, F. et al. ACS Chem. Neurosci. 2016, 7, 737-748; Barbero, G. et al. J. Agric. Food Chem. 2010, 58, 3342-3349; Appendino, G. et al. *J. Med. Chem.* 2002, 45, 3739-3745.)

Starting from a general pharmacophore model of capsaicinoids and capsinoids, efforts have also been devoted to the design and synthesis of antagonists and agonists targeting TRPV1 (transient receptor potential vanilloid 1) for pain relief, resulting in small molecules that bear little resemblance to the natural ligands such as capsaicin and its natural derivative. (For selected examples, see: Mostinski, Y. et al. ACS Chem. Neurosci. 2017, 8, 1688-1696; Parsons, W. H. et al. J. Med. Chem. 2015, 58, 3859-3874; Blum, C. A. et al. J. Med. Chem. 2010, 53, 3330-3348; Ognyanov, V. I. et al. J. Med. Chem. 2006, 49, 3719-3742.)

Topical application of capsaicin typically causes intense burning over the treatment area. Interestingly, capsiate, isolated from a unique variety of sweet chili pepper, and with an ester linkage in place of the secondary amide linkage of capsaicin between the vanilloid head group and the fatty acid tail, therefore a more hydrophobic molecule with one less hydrogen bond to donate, causes essentially no such burning sensation. An ester prodrug formed between the capsaicin phenolic hydroxyl on the vanilloid ring end and a fatty acid causes essentially no irritation when applied topically, presumably the increased hydrophobicity and facilitated dermal uptake of the resulting molecule play a significant role (Singh, C. U. et al. U.S. Pat. No. 7,943,666). Depending on the applications and physiological environment, use of ester functionality, especially a saturated carboxylic acid ester, for the protection of alcohol does sometimes present stability issues. Esters are also susceptible to enzymatic hydrolysis. The stability of an ester depends on the structure of both the acid and the hydroxyl partners. A phenolic ester (ester formed between a carboxylic acid and a phenol) is more labile due to phenol being a better leaving group compared to an aliphatic alcohol (Blay, G. et al. Synthesis 1989, 438-439). In addition to carboxylic esters, prodrugs of capsaicinoids have also been generated between the phenolic hydroxyl group and another hydroxyl containing molecule using a carbonate ester linkage (Jamieson, G. C. et al. U.S. Pat. No. 7,632,519). Carbonate and ether linkages have also been utilized for a transient phenolic alcohol protection using photolytically cleavable molecular partners (Katritzky, A. R. et al. J. Org. Chem. 2003, 68, 9100-9104).

The chemical stability of a carbamate is generally considered to be somewhere between an ester and an amide, and they can be substrates for both esterases and amidases (for a recent review on prodrug approach in drug discovery, see: Rautio, J. et al. Nat. Rev. Drug Discov. 2018, 17, 559-587). Examples of simple aliphatic amines conjugated to a capsaicin molecule with a carbamate linkage, thereby functioning as a simple protecting group for the analgesics, exist in the literature (Boran, A. et al. Curr. Opin. Drug Discov. Devel. 2010, 13(3), 297-309).

Other work in related fields includes that described in U.S. Pat. Nos. 7,632,519, 7,645,767, 7,771,760, 7,943,166, 7,943,666, 8,263,059, 8,263,093, 8,273,390, 8,987,328, as well as U.S. Patent Application Publication Nos. 2014/134261 and 2013/189354.

SUMMARY

The burning and painful sensations associated with capsaicin result from its chemical interaction with sensory neurons. Capsaicin, as a member of the vanilloid family, binds to the vanilloid receptor subtype 1 (TRPV1).

Such undesirable sensations do not occur with compositions of the present disclosure. Unique, non-burning modifications of capsaicin are disclosed through the formation of chemical bonds between capsaicin, a linking moiety and variable functional groups. Further, embodiments herein show unique, non-burning modifications of capsaicin through compounding formulations with capsaicin palmitate and different classes of substances, as well as new drugs that can be made from homogenous compounds made from capsaicin and other hydrophobic molecules in hydroscopic, hydrophobic media or in non-aqueous media, or aqueous media.

A variety of pharmaceuticals and foods have been palmitated. Palmitic acid is the most common cellular fatty acid and is a natural product found in many compounds, including milk, plant congeners and waxes. Palmitated molecules are also ubiquitous as excipients, used in such diverse products as napalm and shampoos.

The use of palmitates includes retinyl palmitate. Palmitate is attached to the alcohol form of vitamin A, retinol, to make vitamin A stable in milk. Ascorbyl palmitate is also a food additive and increases the solubility of vitamin C. Ethylhexyl palmitate is commonly used in cosmetic formulations to provide a dry-slip feel similar to silicone derivatives. Paliperidone palmitate is a long-acting injectable formulation of paliperidone, a dopamine antagonist and 5-HT2A antagonist of the atypical antipsychotic class of medications. Testosterone palmitate is a prodrug of testosterone associated with a long-lasting depot effect and extended duration of action. While palmitated products were designed essentially to enhance absorption, provide nutrients or reduce irritation, capsaicin palmitate is described here for use as a compounding pharmaceuticals in conjunction with substances in order to reduce topical irritation or to enhance the efficacy of capsaicin palmitate. Examples of these compounding substances include cannabidiol, essential oils, waxes, jojoba oil, curcumin, hyaluronic acid, kinetin and nicotinamide.

The present pharmaceutical pro-drug molecules as described herein endow capsaicin with heretofore undescribed linkages to the free alcohol of capsaicin by specific molecules, both conferring hydrophobicity to the molecule as well as steric hinderance to thereby produce and optimize the controlled release kinetics of the capsaicin molecule. These modifications would have the effect of easing or eliminating the burning sensation of capsaicin following topical application.

Esterification of the free hydroxyl group of capsaicin not only introduces steric crowding around the phenolic head group, but also increases the overall hydrophobicity of the molecule. Since the epidermis of the integument is also hydrophobic, the neutralized fatty-acid CP molecule may be readily absorbed. Hydrolysis of an ester bond will occur with diffusion as the molecule encounters moisture layers of the skin.

These molecules are drug conjugates made through linkages such as carbamate, carboxyl esters and diesters. While carbamates have been claimed to produce analgesia, embodiments herein provide a mechanism by which a carbamate or pharmaceutical acceptable derivative of a carbamate is utilized as a connecting moiety to temporarily mask the free hydroxyl group of the capsaicin molecule. More specifically, in embodiments of the invention, carbamates are used as linkers to form prodrugs that can increase the time before the capsaicin molecule is chemically and/or enzymatically hydrolyzed and made free to bind to the TRPV-1 receptor.

Compounds described herein with sustained release properties would be classified as pro-drug molecules. These molecules also modulate or even synergize when linked with other drugs (menthol, morphine, and others). This would define these pro-drug configurations as "sustained release" molecules when devised as structures that are able to provide increased kinetic stability from chemical or enzymatic hydrolysis or metabolic alteration of the capsaicin molecule.

In certain embodiments, amines with one extra functional group such as a carboxyl or a hydroxyl can be used as a handle for attachment of a second molecule, either inert for additional hydrophobicity or a molecule with biological and pharmacological activity (such as a known drug) in order to pursue a polypharmaceutical therapy.

Additionally, the invention herein discloses the use of amine containing heterocycles or heteroaryls as capsaicin prodrug partners in order to modulate the stability of the carbamate linkage. Together these can be summarized in a general formula as shown in FIG. 1.

It was shown that a carboxyl group directly connected to an unsaturated hydrocarbon system is in general less reactive than the one connected to a saturated hydrocarbon system (for comparison of rate of hydrolyzing benzoate vs acetate, see: Seidi, F. et al. Chem. Rev. 2018, 118, 3965-4036). Here, the invention shows that when the free hydroxyl of capsaicin or a related analog is esterified to the carboxyl group of a α,β-unsaturated carboxylic diacid such as fumarate or maleate; the remaining carboxyl group can be esterified with a hydrophobic alcohol to increase the overall hydrophobicity, or attached to another capsaicin to increase the analgesic loading, or other free hydroxyl (OH) bearing molecules. These scenarios are generalized in a formula as shown in FIG. 2.

Esterification of capsaicin with simple hydrophobic carboxylic acids has been shown to increase dermal uptake of the analgesics and reduce burning sensation, presumably due to the increased hydrophobicity of the overall modalities. Here, in an embodiment, capsaicin esters can be prepared using very long chain ($>C_{20}$) fatty acids (VLCFAs). Some of these VLCFAs have been identified from the seed oils of natural plant origin (Li, X. et. al. Nature Plants 2018). These natural fatty acids usually contain an extra hydroxyl group which can be used as a handle for the attachment of extra capsaicin molecule, or another molecule of interest for polypharmaceutical therapeutics purpose. These are generalized in a formula as shown in FIG. 3.

Building on the prodrug concept and increasing capsaicin loading, in another embodiment, esters of capsaicin can be prepared with symmetrical saturated carboxylic diacids. This is summarized in formulas as shown in FIGS. 4 and 4A.

The current invention discloses the design and synthesis of a series of pro-drugs of capsaicin. These pro-drug molecules endow capsaicin with improved uptake and delivery under different physiological conditions such as pain, and for various applications, such as topical administration formulations.

The current invention also discloses the design and synthesis of a series of drugs that are designed as compounded drug formulations. These include different classes of chemicals, oils, drugs, waxes and natural products. These formulations are combined as mixtures with capsaicin palmitate without chemical bonds in order to make drug designs that mitigate capsaicin burning at the epidermis such and in which none of the components are joined by covalent, ionic or hydrogen bonding. According to embodiments of the invention, capsaicin palmitate and capsaicin palmitate with compounded drugs are formulated for topical epidermal applications, oral (lingual, buccal), sterile injectable, inhalant, patch or plaster forms, or iontophoretic ways of administration.

Accordingly, aspects of the invention include Capsaicin/ Capsaicinoid drugs administered through topical vehicles, sterile injectable vehicles, patch or plaster vehicles, oral, inhalants or sublingual, iontophoretic or buccal formulations.

Aspects of the invention include Capsaicin/Capsaicinoid drugs that are comprised of: (1) molecules that provide enhanced hydrophobicity of capsaicin due to covalent linkage with hydrocarbon moieties; and (2) molecules capable of cleavage to capsaicin or capsaicinoid compounds following dermal enzymatic or hydrolytic de-esterification.

Aspects of the invention further include compounds made with modifications of capsaicin, including the following representative classes of compounds: (1) Capsaicin linked to different moieties by a carbamate linker (e.g., 3hydroxymethyl pyrrolidine, 4-aminobutanol, 3-pyrrolidinyl acetic acid, 1-piperazine propanoic acid, prolinol, 3-piperidinyl methanol, proline, nipecotic acid, morpholine, 4piperidinone, 3,3-difluoropyrrolidine, 2-pyrrolidinone, pyrrole-2-carboxylate, 3-carboxy1H-pyrazole, 2-pyridone, pyridazinone) on the vanilloid ring-end of the capsaicin molecule; (2) Capsaicin linked to different moieties by ester bond formation with α,β-unsaturated carboxylic acid (e.g., fumarate, maleate, acetylene dicarboxylate, terephthalate, 4,5-difluorophthalic acid) on the vanilloid ring-end of the capsaicin molecule; (3) Capsaicin linked to different moieties by ester bond formation with very long chain carboxylic acids (>C20) on the vanilloid ring-end of the capsaicin molecule; and (4) Capsaicin linked to different moieties by ester bond formation with symmetrical carboxylic diacids (e.g., 1,4-cyclohexane dicarboxylic acid, 1,3-cyclohexane dicarboxylic acid, cyclopropane 1,1-dicarboxylic acid, succinic acid, adipic acid)) on the vanilloid ring-end of the capsaicin molecule.

In another aspect, in an alternative to a carbamate linkage, the free phenolic hydroxyl group of capsaicin may be esterified with a carboxylic acid to generate a capsaicin prodrug with an ester linkage. The carboxylic acid is a α,β-unsaturated for the purpose of generating a more hydrolysis resistant ester bond (for example, alkenyl or benzoic acids). In addition, it is preferably a carboxylic di-acid with the potential of using the second carboxyl group for increasing capsaicin loading, or to introduce a hydrophobic molecule to increase overall hydrophobicity of the prodrug, or a molecule with pharmaceutical property to modulate the prodrug pharmacology. The ester forming carboxylic acid can also be a long chain aliphatic acid. In this case, the overall number of carbon of the acid is over 20.

Aspects include formulations of drugs compounded with capsaicin palmitate or derivatives or analogs of capsaicin palmitate as pharmaceutical mixtures.

Aspects also include methods for using and/or making any of the compounds and/or compositions disclosed in any other aspect. Specific methods included are (1) methods of synthesis of hydrophobic drugs cleaved to produce timed release of capsaicin or capsaicinoid molecules from a linker molecule to carboxylic groups; and (2) methods of formulating compounded drugs with capsaicin palmitate or derivative or analogs of capsaicin palmitate.

BRIEF DESCRIPTION OF THE DRAWINGS

The accompanying drawings illustrate certain aspects of embodiments of the present invention and should not be used to limit the invention. Together with the written description the drawings explain certain principles of the invention.

BEST MODE FOR CARRYING OUT THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

As used herein, the term "prodrug" is meant to indicate a biologically inactive precursor compound which may undergo a chemical conversion in the body to produce an active pharmacological agent.

The following drugs are designed to optimize the kinetics of the release of capsaicin. These compounds with capsaicin attached thus inhibit the binding of capsaicin to its receptor (TRPV1), and release the capsaicin molecule over time. The different carbamate moieties, molecular linkages, and other non-carbamate, noncapsaicin linking or parent structures are designed to release capsaicin, or to allow the cleavage of capsaicin from the structure, over different dissociation time periods, under different physiological environments, and for different application and administration formats.

Carbamates

The starting structure for these compounds is capsaicin (R3 in the structure below, and abbreviated Cpsn or CPS subsequently herein) and a carbamate functional group incorporated in a small molecular linking moiety (generalized as R2, R1), resulting in the protection of the hydroxyl group and as a capsaicin prodrug:

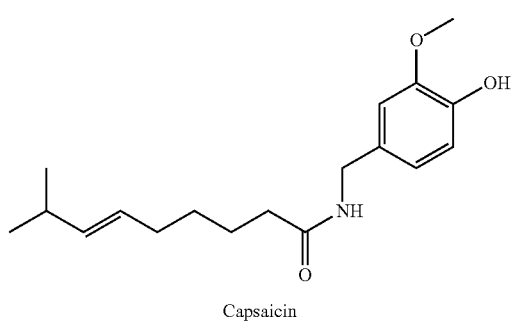

Capsaicin

-continued

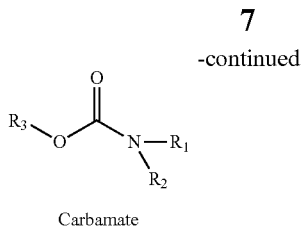

Carbamate

Figure 1:
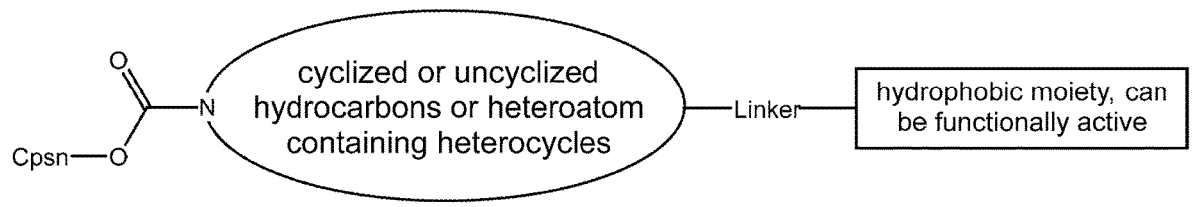
FIG. 1 is a schematic diagram showing a mechanism by which a linker is attached to nitrogenous cyclized or uncyclized hydrocarbons or heteroatom containing heterocycles to form a carbamate linkage with the free phenolic hydroxyl group of capsaicin.

FIG. 1 shows a general format by which a linker is attached to nitrogenous cyclized or uncyclized hydrocarbons or a heteroatom containing heterocycles to form a carbamate linkage with the free phenolic hydroxyl group of capsaicin. In such a case, the other end of the linker is attached to a hydrophobic molecule or a molecule with biological or physiological activities. In another embodiment, capsaicin is attached, by way of its free phenolic hydroxyl group, to a hydrocarbon or hetero hydrocarbon or heteroaryl moiety of varied structural complexity through a carbamate bridge. These capsaicin analogs are designed as simple prodrugs with the carbamate functionality as the protective group with modulated stabilities (see formulas VII to IX, and X for example).

In one embodiment of the present invention, a method of synthesizing a capsaicin derivative chemical compound is provided using a process for the preparation of molecules with a general chemical structure as shown in Formula I:

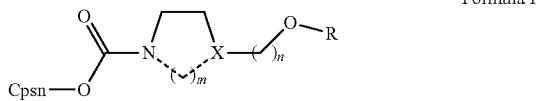

Formula I wherein X=C or N;
R=H, or R=C(O)R' where R'=1 to 20 hydrocarbons, straight, branched, cyclized, saturated or unsaturated (examples include but are not limited to: palmitate, oleate, abietic acetate, etc.);
when X is a carbon (C): m=0 to 3, and n=0 to 2; in addition, when m=1 or 3, the carbon X can be both racemic and chiral; and when X is a nitrogen (N): m=2, and n=2.

Scheme 1 depicts an exemplary synthetic pathway to the prodrug of Formula I, wherein EDC is an exemplary coupling reagent, 1-Ethyl-3(3-dimethylaminopropyl)carbodiimide.

Scheme 1

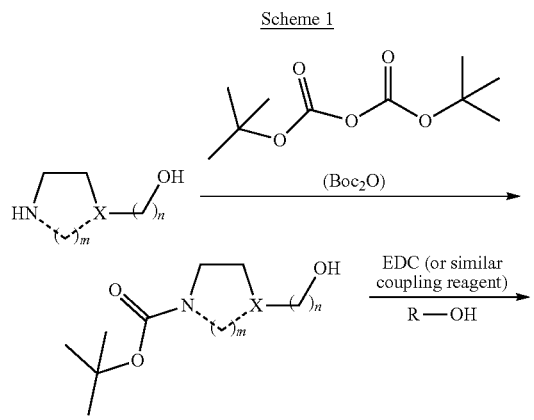

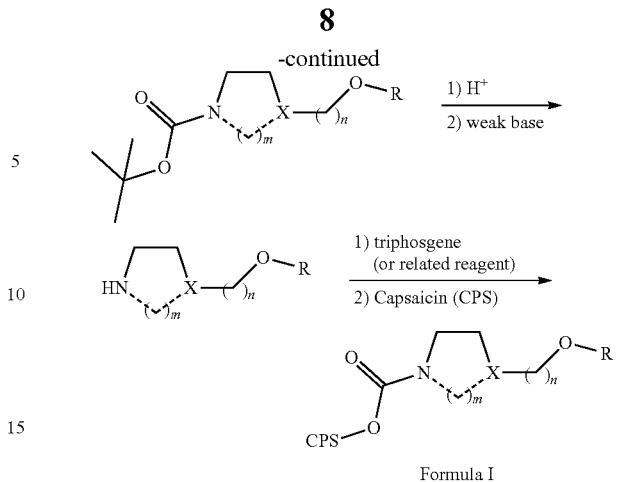

Formula I

In another embodiment of the present invention, a method (Scheme 2) of synthesizing a capsaicin derivative chemical compound is provided using a process for the preparation of molecules with a general chemical structure as shown in Formula II:

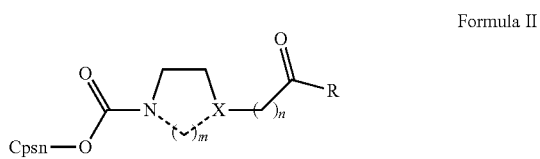

Formula II wherein X=C or N;
R=OH, or R=OR' where R'=1 to 20 hydrocarbons, straight, branched, cyclized, saturated or unsaturated, and/or R' is chosen from molecules with analgesic properties or other pharmacological properties, such as capsaicin, cannabidiol etc.
when X is a carbon (C): m=0 to 3, and n=0; in addition, when m=1 or m=3, the carbon X can be both racemic and chiral; and
when X is a nitrogen (N): m=2, n=0 to 2; in addition, when X=N, m=2, and n=0, then R=1 to 20 hydrocarbons, straight, branched, cyclized, saturated or unsaturated (examples included but not limited to: palmitate, oleate, abietic acetate, etc.).

See Scheme 2 depicts an exemplary synthetic pathway to the prodrug of Formula II.

Scheme 2

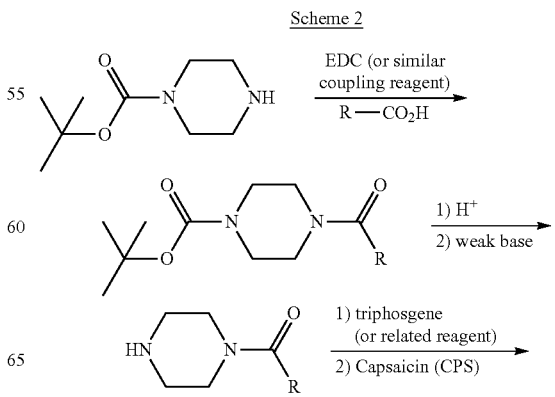

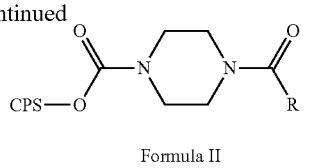

Formula II

In another embodiment of the present invention, a method of synthesizing a capsaicin derivative chemical compound is provided using a process for the preparation of molecules with a general chemical structure as shown in Formula III:

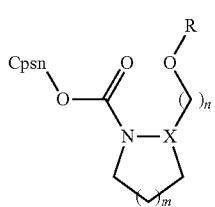

Formula III

Wherein X=C;

R=H, or R=C(O)R' where R'=1 to 20 hydrocarbons, straight, branched, cyclized, saturated or unsaturated (examples include but are not limited to: palmitate, oleate, abietic acetate, etc.); X is a methine (CH), and can be both racemic and chiral; and m=1 to 2, n=1 to 2.

Compounds of Formula III can be prepared in a similar manner as in Scheme 1.

In another embodiment of the present invention, a method of synthesizing a capsaicin derivative chemical compound is provided using a process for the preparation of molecules with a general chemical structure as shown in Formula IV:

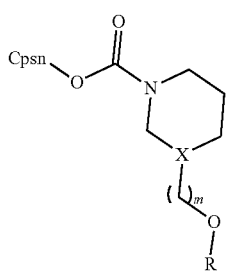

Formula IV wherein X=C;

R=H, or R=C(O)R' where R'=1 to 20 hydrocarbons, straight, branched, cyclized, saturated or unsaturated (examples include but are not limited to: palmitate, oleate, abietic acetate, etc.); X is a methine (CH), can be both racemic and chiral; and m=0 to 2.

Compounds of Formula IV can be prepared in a similar manner as in Scheme 1.

In another embodiment of the present invention, a method of synthesizing a capsaicin derivative chemical compound is provided using a process for the preparation of molecules with a general chemical structure as shown in Formula V:

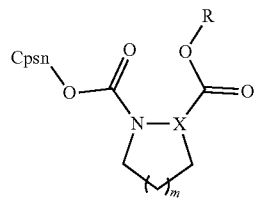

Formula V wherein X=C;

R=H, R=1 to 20 hydrocarbons, straight, branched, cyclized, saturated or unsaturated, and/or R is chosen from molecules with analgesic properties or other pharmacological properties, such as capsaicin, cannabidiol, etc.;

X is a methine (CH), can be both racemic and chiral;

and m=1 to 2.

In addition, X is a methine (CH), can be both racemic and chiral;

m=1 to 2.

Compounds of Formula V can be prepared in a similar manner as in Scheme 2.

In another embodiment of the present invention, a method of synthesizing a capsaicin derivative chemical compound is provided using a process for the preparation of molecules with a general chemical structure as shown in Formula VI:

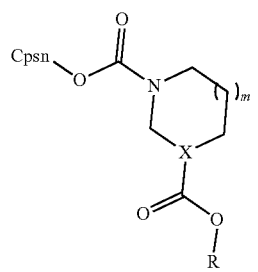

Formula VI wherein X=C;

R=H, or R=1 to 20 hydrocarbons, straight, branched, cyclized, saturated or unsaturated, and/or R is chosen from molecules with analgesic properties or other pharmacological properties, such as capsaicin, cannabidiol, etc.;

X is a methine (CH), can be both racemic and chiral;

and m=1 to 2.

Compounds of Formula VI can be prepared in a similar manner as in Scheme 2.

In another embodiment of the present invention, a method of synthesizing a capsaicin derivative chemical compound is provided using a process for the preparation of molecules with a general chemical structure as shown in Formula VII:

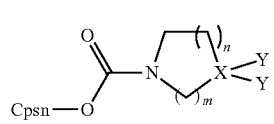

Formula VII wherein X=C or O, or X=sp3 or sp2 hybridized carbon (C); m=1 to 2, n=1 to 2; Y=F or O (ketone); and when m=2, n=1 or 2, X can be an oxygen (O), in which case Y can be regarded as the oxygen lone pairs.

Scheme 3 depicts an exemplary synthetic pathway to the prodrug of Formula VII,

Scheme 3

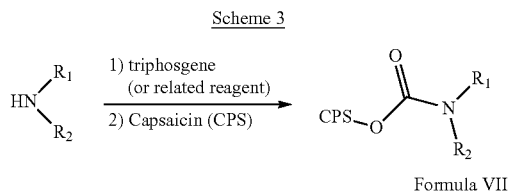

Formula VII

In another embodiment of the present invention, a method of synthesizing a capsaicin derivative chemical compound is provided using a process for the preparation of molecules with a general chemical structure as shown in Formula VIII:

Formula VIII

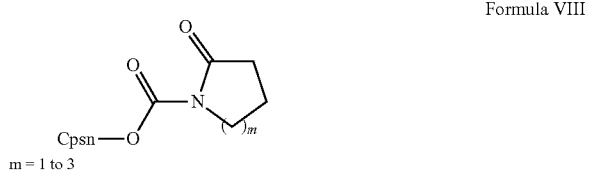

m = 1 to 3

Compounds of Formula VIII can be prepared in a similar manner as in Scheme 3.

In another embodiment of the present invention, a method of synthesizing a capsaicin derivative chemical compound is provided using a process for the preparation of molecules with a general chemical structure as shown in Formula IX:

Formula IX

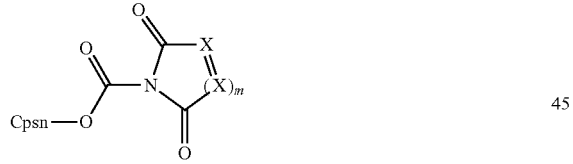

wherein X=CH2 or CH (when m=1), m=1 to 3; and when m=1, the bond between the two X atoms can be either a single or a double bond.

Compounds of Formula IX can be prepared in a similar manner as in Scheme 3.

In another embodiment of the present invention, a method of synthesizing a capsaicin derivative chemical compound is provided using a process for the preparation of molecules with a general chemical structure as shown in Formula X:

Formula X

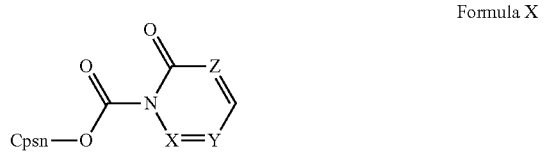

X, Y, and Z can be all carbons, or up to two nitrogen atoms, examples include:

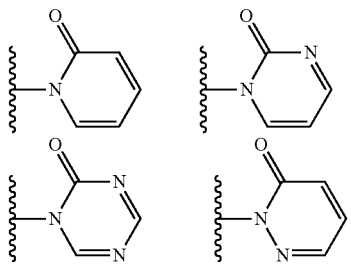

Compounds of Formula X can be prepared in a generally similar manner as in Scheme 3, using appropriately functionalized HNR1 R2.

Unsaturated Carboxylic Acid Esters

Figure 2:
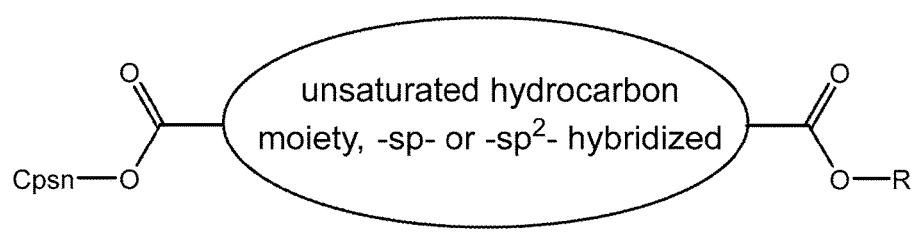
FIG. 2 is a schematic diagram showing a capsaicin joined to a carboxyl group directly connected to an unsaturated hydrocarbon moiety.

In other embodiments, as shown in FIG. 2, a capsaicin molecule is attached to a α,β-unsaturated di-carboxylic acid by way of its phenolic hydroxyl group to form an ester bond. The remaining carboxylic acid of the unsaturated moiety can be esterified to increase overall hydrophobicity of the molecule, or be attached to another molecule of capsaicin for increased loading, or be attached to a molecule with analgesic property or other pharmacological property for modulating the overall pharmacological properties of the molecule.

The starting structures for these compounds are capsaicin and a carboxylate functional group used as a linker between capsaicin and a hydrophobic molecule or a functionally active moiety attached using the remaining carboxylate of the unsaturated linking bridge (designated as R below):

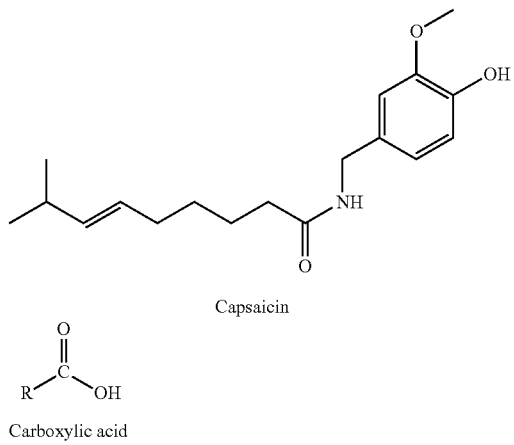

Capsaicin

Carboxylic acid

In embodiments, R may comprise: R=H, or R=1 to 20 hydrocarbons, straight, branched, cyclized, saturated or unsaturated, and/or R is chosen from molecules with analgesic properties or other pharmacological properties, such as capsaicin, cannabidiol, etc.

In order to create more hydrophobicity and/or an "add-on" pharmacology, in embodiments, the di-carboxyl containing unsaturated molecular modules such as fumarate, maleate, and benzoate dicarboxylic acids can be used. A carboxylic acid is an organic compound containing carboxyl group (COOH) attached to an alkyl or aryl group. The general formula of a carboxylic acid is Ar/R—COOH where Ar/R represents the aryl or alkyl group attached. In carboxylic acids, three of the four bonds of a carboxyl carbon atom are to two oxygen atoms:

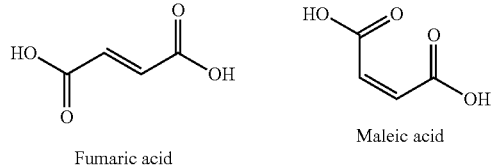

Fumaric acid     Maleic acid

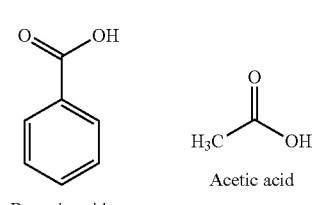

Benzoic acid     Acetic acid

A carboxyl group directly connected to unsaturated hydrocarbon system is less reactive than the one connected to a saturated hydrocarbon system (for comparison of rate of hydrolyzing benzoate vs. acetate, see: Seidi, F. et al. Chem. Rev. 2018, 118, 3965-4036). This scenario is summarized in FIG. 2, wherein R=H, or R=1 to 20 hydrocarbons, straight, branched, cyclized, saturated or unsaturated, and/or R is chosen from molecules with analgesic properties or other pharmacological properties, such as capsaicin, cannabidiol, etc.

Examples of unsaturated hydrocarbon moiety can be two carbon based, such as.

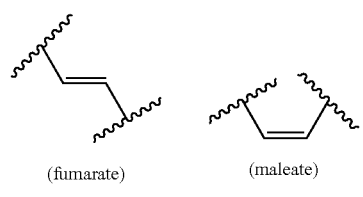

(fumarate)     (maleate)

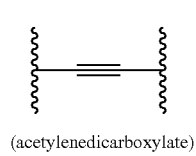

(acetylenedicarboxylate)

Examples of the unsaturated hydrocarbon moiety can also be benzene dicarboxylic acid based, with up to 4 substitutions and up to 6 carbons on each substitution on the benzene ring. These side chain substitutions can be straight, branched, or small rings. Substitutions can also be heavy atoms such as halogens (F, Cl, Br), oxygen (hydroxy, alkoxy) or nitrogen based; and various combinations among heavy atoms and with hydrocarbon side chains. Examples include but are not limited to:

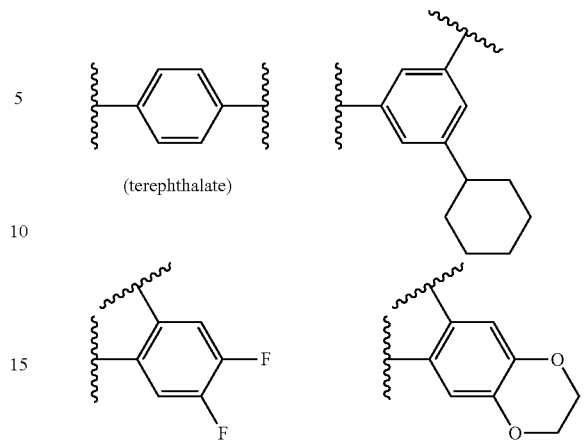

(terephthalate)

A generalized synthesis of these α,β-unsaturated di-carboxylic acid esters is shown in Scheme 4, using fumarate di-ester as an example.

Scheme 4

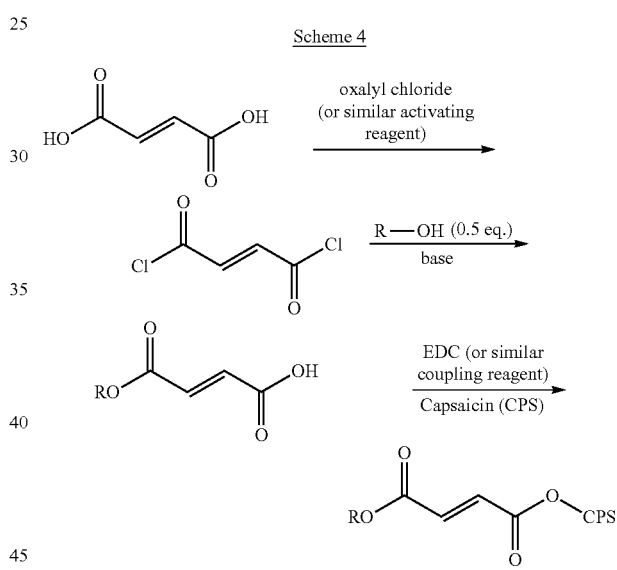

Esters Formed With Very Long Chain Fatty Acids (>C20; VLCFAs)

Figure 3:
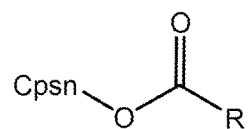
FIG. 3 is a schematic diagram showing a capsaicin molecule esterified to a very long chain fatty acid (VLCFA) by way of its phenolic hydroxyl group.

In embodiments, shown in FIG. 3, a capsaicin molecule is esterified to a very long chain fatty acid (VLCFA) by way of its phenolic hydroxyl group, wherein R=a hydrocarbon chain of over 20 carbon atoms in length. These types of fatty acids have been isolated from seed oils of natural plant origin, such as castor oil from the seeds of the *Ricinus communis* plant, which can account for up to 50% of the seed oil by weight (Mubofu, E. B. Sustain Chem Process (2016) 4: 11. https://doi.org/10.1186/s40508-016-0055-8). In embodiments, the hydroxyl groups usually present in fatty acids can be used as handles for attachment of more capsaicin molecules for increased analgesic loading, or masked chemically (i.e., as small alkoxyls) to increase hydrophobicity of the molecules, or attachment of another molecule of interest.

Saturated Carboxylic Acid Diesters

Figure 4:
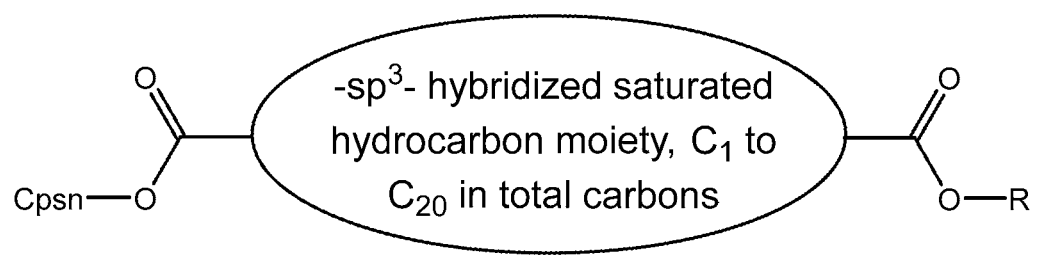
FIG. 4 is a schematic diagram showing a capsaicin molecule attached to a saturated hydrocarbon moiety with two carboxylic acid functional groups by way of its phenolic hydroxyl group to form an ester bond.

FIG. 4 depicts a capsaicin molecule attached to a saturated hydrocarbon moiety with two carboxylic acid functional groups by way of its phenolic hydroxyl group to form an ester bond, wherein R=1 to 20 hydrocarbons, straight, branched, cyclized, saturated or unsaturated; or R=molecules with analgesic properties or other pharmacological properties, such as capsaicin, cannabidiol, etc.

Alternatively, R=H (except when the central hydrocarbon moiety is a straight chain, in which case reference is made to FIG. 4A below). The central hydrocarbon moiety can be straight, branched, or cyclized carbon chains containing up to 20 carbons. The remaining carboxylic acid of the diacid moiety may be esterified to increase overall hydrophobicity of the molecule, or may be attached to another capsaicin for increased loading, or may be attached to a selected molecule with an analgesic property or other pharmacological property for potential modulation of the overall pharmacological profile.

Figure 4A:
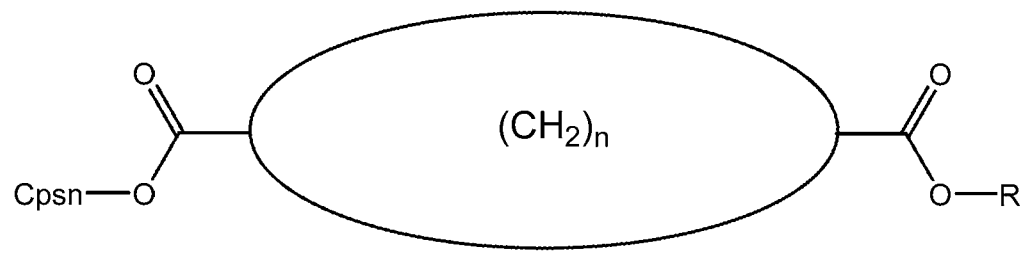
FIG. 4A is a variant of the compound of FIG. 4, when the central saturated hydrocarbon moiety is a straight carbon chain.

When the central saturated hydrocarbon moiety is a straight carbon chain, the molecule can be depicted with a general structure as shown in FIG. 4A, wherein n=0 to 20 and R=H, when n is 0-1, or 4-20, or R=1 to 20 hydrocarbons, straight, branched, cyclized, saturated or unsaturated, and/or R is chosen from molecules with analgesic property or other pharmacological property such as capsaicin, cannabidiol, etc.

Representative central straight chain linkers include but are not limited to oxalate (n=0), succinate (n=2), and adipic acetate (n=4).

The current invention discloses the design and synthesis of a series of pro-drugs of capsaicin, which endow capsaicin with improved skin and cell membrane penetration, making possible a slower release of the analgesics and thereby ease or eliminate the burning sensation as it passes these biological barriers.

These pro-drug molecules are comprised of capsaicin attached to a hydrocarbon or hetero hydrocarbon or heteroaryl moiety through a carbamate bridge (FIG. 1), α,β-unsaturated carboxylic acid esters (FIG. 2), very long chain fatty acid esters (FIG. 3), or symmetrical dicarboxylic acid esters (FIG. 4).

These structures can be expanded on by adding additional elements in a similar format. Different forms of the compounds (e.g., stoichiometry, crystals, salts, formulations, purity characteristics, isomers, indications, dosing protocols, combinations, processes for preparing, etc.) may be considered.

Formulations

Pharmaceutical formulations are referred to here as compounded mixtures of pharmaceutically active ingredients. Usually a compounded formulation contains selected inactive ingredients such as water, oil, surfactants, emulsifiers, stabilizers, chelators, preservatives, and pH-adjusting agents. The active ingredients may or may not be solubilized in the carrier vehicle. Mixing pharmaceuticals typically combines two or more components together by agitation, shear or mixers. The final product of mixture usually contains uniform or homogeneous mixture of both components.

The following formulations are made from mixtures with palmitated capsaicin. The following drugs are designed to optimize the analgesic efficacy and to minimize dermal irritation with the use of capsaicin with different classes of compounds. These compounds do not attach to capsaicin but may mitigate the dermal irritation produced by capsaicin.

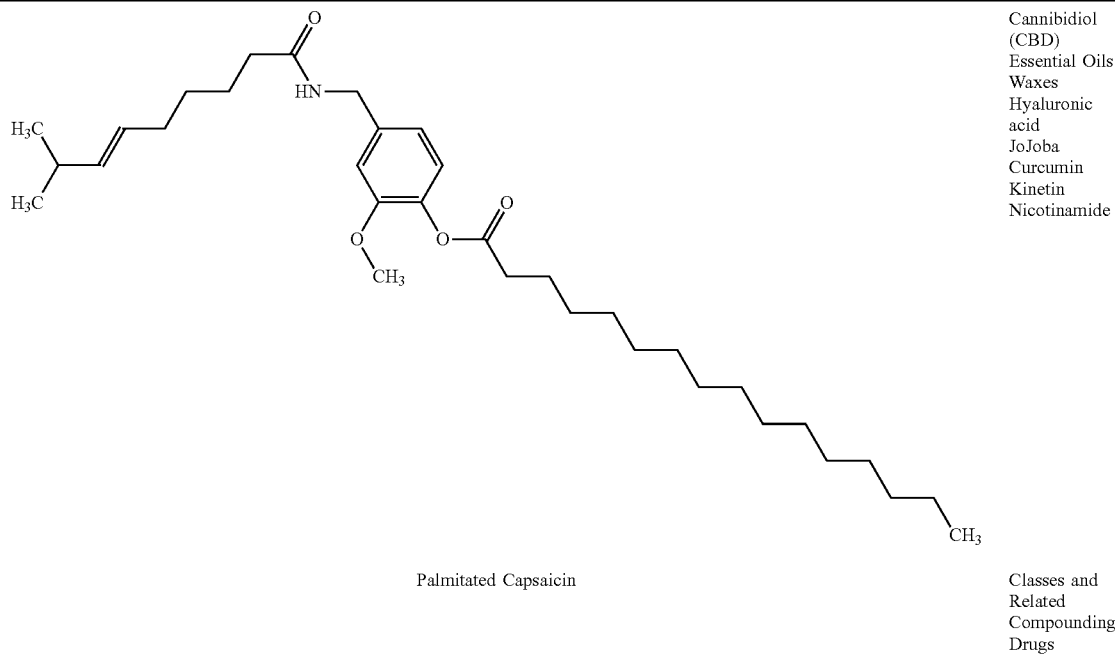

Palmitated Capsaicin

Cannibidiol (CBD)
Essential Oils
Waxes
Hyaluronic acid
JoJoba
Curcumin
Kinetin
Nicotinamide Classes and Related Compounding Drugs Formulations according to embodiments of the invention can include a mixture or a structure such as a capsule, a pill, tablet, or an emulsion, prepared according to a specific procedure (called a "formula"). Formulations are important for creating medicines, since they are essential to ensuring that the active part of the drug is delivered to the correct part of the body, in the right concentration, and at the right rate. Competently designed formulations for particular applications are safer, more effective, and more economical than any of their components used singly.

Formulations of the invention include capsaicin bonded to any palmitic acid species with 1-20 carbon chains. Palmitic acid, or hexadecanoic acid, is one of the most common saturated fatty acids found in animals, plants, and microorganisms. As its name indicates, it is a major component of the oil from the fruit of oil palms (palm oil). Excess carbohydrates in the body are converted to palmitic acid. Palmitic acid is the first fatty acid produced during fatty acid synthesis and is the precursor to longer fatty acids. As a consequence, palmitic acid is a major body component of animals.

Formulations of embodiments of the invention also include capsaicin bonded to any oleic acid species with 1-20 carbon chains. Oleic acid is an unsaturated fatty acid that is the most widely distributed and abundant fatty acid in nature. It is used commercially in the preparation of oleates and lotions, and as a pharmaceutical solvent.

Additionally, embodiments of the invention include formulations with capsaicin bonded to any linoleic acid species with 1-20 carbon chains such as formulations with capsaicin bonded to any ethylhexyl palmitate (octyl palmitate) or 2ethylhexyl species with 1-20 carbon chains.

Formulations of the present invention can include any one or more of the substances listed below compounded with capsaicin palmitate.

1. Cannibidiol (CBD): (2-[(6R)-6-Isopropenyl-3-methyl-2-cyclohexen-1yl]-5-pentyl-1,3-benzenediol) and Physically-Modified Derivatives or Precursors of CBD.

These are compounds extracted from the marijuana plant.

Cannabidiol is an cannabinoid that is cyclohexene which is substituted by a methyl group at position 1, a 2,6-dihydroxy-4-pentylphenyl group at position 3, and a prop-1-en-2-yl group at position 4. It has a role as a plant metabolite. It is a member of resorcinols, an olefinic compound and a phytocannabinoid.

Cannabidiol is a phytocannabinoid derived from *Cannabis* species, which is devoid of psychoactive activity, with analgesic, anti-inflammatory, antineoplastic and chemopreventive activities. Upon administration, cannabidiol (CBD) exerts its anti-proliferative, anti-angiogenic and pro-apoptotic activity through various mechanisms, which likely do not involve signaling by cannabinoid receptor 1 (CB1), or vanilloid receptor TRPV1. CBD stimulates endoplasmic reticulum (ER) stress and inhibits AKT/mTOR signaling, thereby activating autophagy and promoting apoptosis. In addition, CBD enhances the generation of reactive oxygen species (ROS), which further enhances apoptosis. This agent also upregulates the expression of intercellular adhesion molecule 1 (ICAM-1) and tissue inhibitor of matrix metalloproteinases-1 (TIMP1) and decreases the expression of inhibitor of DNA binding 1 (ID-1). This inhibits cancer cell invasiveness and metastasis. CBD may also activate the transient receptor potential vanilloid type 2 (TRPV2), which may increase the uptake of various cytotoxic agents in cancer cells. The analgesic effect of CBD is mediated through the binding of this agent to and activation of CB2 located on immune cells such as macrophages and some nerve terminals.

Although the exact mechanism and magnitude of effects of THC and CBD are not fully understood, CBD has been shown to have analgesic, anticonvulsant, muscle relaxant, anxiolytic, neuroprotective, anti-oxidant, and anti-psychotic activity. This wide variety of effects is likely due to its complex pharmacological mechanisms. In addition to binding to CB2 receptors of the endocannabinoid system, there is evidence that CBD activates 5-HT1A serotonergic and TRPV1-2 vanilloid receptors, antagonizes alpha-1 adrenergic and μ-opioid receptors, inhibits synaptosomal uptake of noradrenaline, dopamine, serotonin and gaminobutyric acid and cellular uptake of anandamide, acts on mitochondria Ca2 stores, blocks low-voltage-activated (T-type) Ca2 channels, stimulates activity of the inhibitory glycine-receptor, and inhibits activity of fatty amide hydrolase.

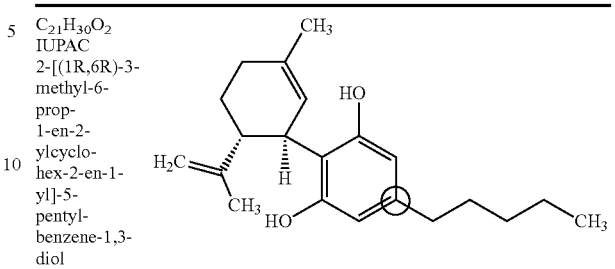

$C_{21}H_{30}O_2$
IUPAC
2-[(1R,6R)-3-methyl-6-prop-1-en-2-ylcyclohex-2-en-1-yl]-5-pentyl-benzene-1,3-diol Synonyms include cannabidiol, 13956-29-1, (−)-Cannabidiol, (−)-transCannabidiol, CBD, Epidiolex, UNII-19GBJ60SN5, (−)-trans-2-p-Mentha-1,8-dien-3-yl-5pentyl-resorcinol, delta1(2)-trans-Cannabidiol, (−)-CBD, GWP42003-P, 19GBJ60SN5, CHEMBL190461, CHEBI: 69478, QHMBSVQNZZTUGM-ZWKOTPCHSA-N, 1,3-Benzenediol, 2-(3-methyl-6-(1-methylethenyl)-2-cyclohexen-1-yl)-5-pentyl-(1R-trans)-2-[(1R,6R)-3-methyl-6-prop-1-en-2-ylcyclohex-2-en-1-yl]-5-pentylbenzene-1,3-diol, (1'R,2'R)-5'-methyl-4-pentyl-2'-(prop-1-en-2-yl)-1',2', 3',4'-tetrahydrobiphenyl-2,6-diol, Resorcinol, 2-p-mentha-1, 8-dien-3-yl-5-pentyl-, (−)-(E)-Cannabidiol [USAN]. Related compounds include: Cannabidiolic acid (CBDa), Cannabigerol (CBG), Cannabichromene (CBC), Cannabielsoin (CBE), Cannabicyclol (CBL), Cannabicitran (CBT).

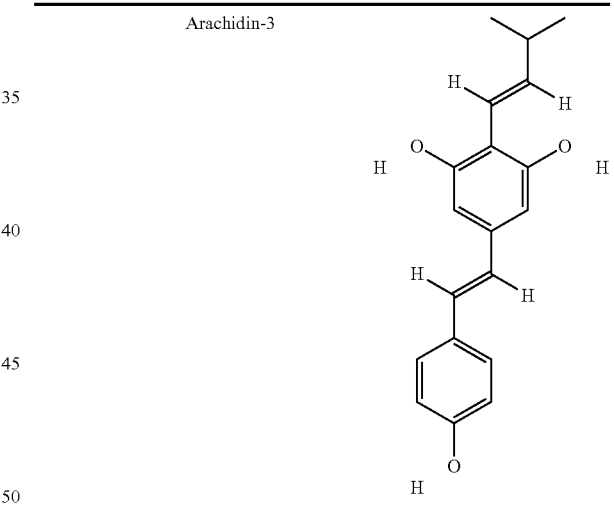

Arachidin-3

2. Essential and/or Essence Oils

Essential oils are compounds extracted from plants. The oils capture the plant's scent and flavor, also called its "essence." Unique aromatic compounds give each essential oil its characteristic essence. Essential oils are claimed to have medicinal qualities, including aromatherapy, treating skin conditions, soothing muscle inflammation, to name a few.

Examples of essential oils that can be formulated with capsaicin palmitate, include any one or more of the following (IUPAC names provided):

*Arctium lappa*, ext. extractives and their physically modified derivatives such as tinctures, concretes, absolutes, essential oils, oleoresins, terpenes, terpenefree fractions, distillates, residues, etc., obtained from *Arctium lappa*, Compositae.

Balsams, tolu, ext. extractives and their physically modified derivatives. This essential oil is comprised primarily of resins, essential oils, and usually cinnamic and benzoic acids, derived from myroxylon balsamum, leguminosae.

*Evernia furfuracea*, ext. extractives and their physically modified derivatives such as tinctures, concretes, absolutes, essential oils, oleoresins, terpenes, terpene-free fractions, distillates, residues, etc., obtained from *Evernia furfuracea*, usnea.

*Evernia prunastri*, ext. extractives and their physically modified derivatives such as tinctures, concretes, absolutes, essential oils, oleoresins, terpenes, terpene-free fractions, distillates, residues, etc., obtained from *Evernia prunastri*, usneace.

Grapefruit, ext. Extractives and their physically modified derivatives such as tinctures, concretes, absolutes, essential oils, oleoresins, terpenes, terpene-free fractions, distillates, residues, etc., obtained from *Citrus paradisi*.

Lemon, ext. extractives and their physically modified derivatives such as tinctures, concretes, absolutes, essential oils, oleoresins, terpenes, terpene-free fractions, distillates, residues, etc., obtained from *Citrus limonum*, Rutaceae.

Orange, sweet, ext. extractives and their physically modified derivatives such as tinctures, concretes, and absolutes.

Star anise, *Illicium verum*, ext. extractives and their physically modified derivatives such as tinctures, concretes, absolutes, essential oils, oleoresins, terpenes, terpene-free fractions, distillates, residues, etc., obtained from *Illicium verum*, Illiciaceae.

olive, patchouli, rose, rosehip, sandalwood, sunflower, vetiver, ylang-ylang, and vegetable oils.

Formulations of embodiments of the invention can include any one or more botanical antimicrobial compositions described for example in U.S. Published Patent Application No. 2016/374352, which provides antimicrobial compositions comprising mixtures of botanical extracts, synthetic antimicrobial agents and essential oils which do not rely solely upon alcohol to produce their antimicrobial effects.

3. Waxes

Wax (wax esters). Waxes and waxy substances, jojoba, reaction products with di-Bu phosphonate, fragrance products, wax blends and cosmetics can be used in formulations of embodiments of the invention. Waxes are sometimes used for timed release depot mechanisms and controlled-release delivery systems having a stable-release pattern. Waxes for example described in U.S. Pat. No. 5,656,296 can be used in formulations of the invention, such as natural waxes and/or synthetic waxes.

4. HYALURONIC ACID

Hyaluronic acid, ion (neg.); Hyaluronic acid sodium salt (a natural highviscosity mucopolysaccharide with alternating beta (1-3) glucuronide and beta (1-4) glucosaminidic bonds); N,N,N-tributyl-1-butanaminium; 1-Butanaminium; N,N,Ntributyl-; hyaluronate (9Cl); Hyaluronic acid tetrabutylammonium salt; Tetrabutylammonium hyaluronate or Thiooctoyl hyaluronic acid sodium salt; and related compounds, such as:

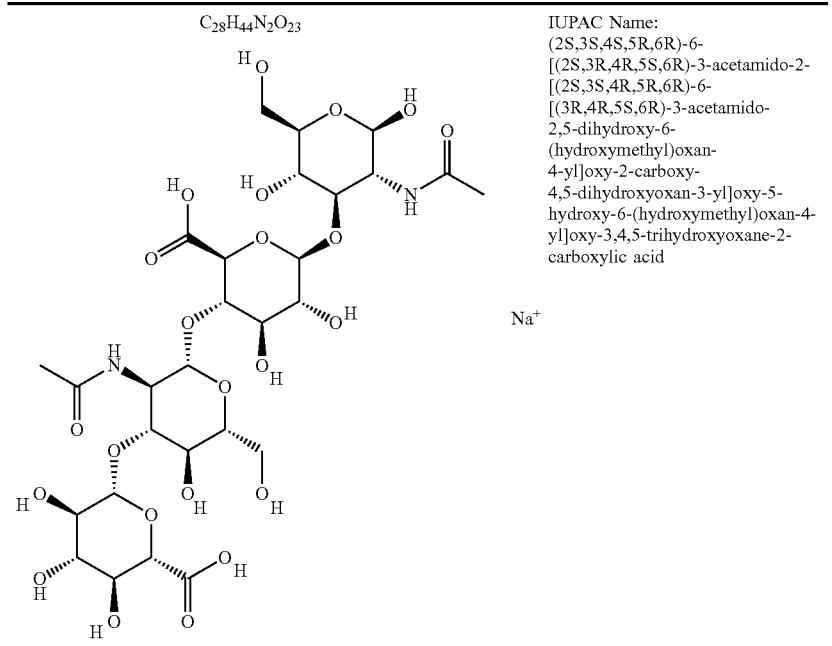

$C_{28}H_{44}N_2O_{23}$

IUPAC Name:
(2S,3S,4S,5R,6R)-6-[(2S,3R,4R,5S,6R)-3-acetamido-2-[(2S,3S,4R,5R,6R)-6-[(3R,4R,5S,6R)-3-acetamido-2,5-dihydroxy-6-(hydroxymethyl)oxan-4-yl]oxy-2-carboxy-4,5-dihydroxyoxan-3-yl]oxy-5-hydroxy-6-(hydroxymethyl)oxan-4-yl]oxy-3,4,5-trihydroxyoxane-2-carboxylic acid Na⁺

*Eucalyptus maculata citriodora*, ext. extractives and their physically modified derivatives such as tinctures, concretes, absolutes, essential oils, oleoresins, terpenes, terpene-free fractions, distillates, residues, etc., obtained from *Eucalyptus maculata citriodora, myrtaceae*.

Others: almond, argan, avocado, bergamot, black seed, borage, cannabidiol oil, cedar, chamomile, clary sage, coconut, emu, flaxseed, frankincense, grape seed, hemp seed, lavender, lemongrass, marjoram, neroli, palm, pumpkin, Synonyms for hyaluronic acid include: Healon, Hyaluronate Sodium, Hyalgan, Hyalurone sodium, Equron (veterinary), Synacid (veterinary), Hyaluronic acid, sodium salt, Hyaluronic acid sodium, Nrd101, CCRIS 4127, Hyaluronate Sodium, SI-4402, SL-1010, Kopuron, Arthrease, Cystistat, Hyalart, Hyalein, Hyalovet, Hyladerm, Khionat, Monovisc, Nidelon, Orthovisc, Ostenil, Provisc, Sinovial, Supartz, Suvenyl, Hyasol, Hyladerm Khionat, Hyaluronsan HA-LQ, Bio Hyaluro 12, EUFLEXXA injection, EUFLEXXA, Sodium hyaluronate HMW, UNII-YSE9PPT4TH, Synacid, Equron, Chlamyhyaluronic acid sodium salt, Suvenyl (TN), SL 1010, Hyalauronic Acid 99%, YSE9PPT4TH, D07BSE, DOJ4NF, DOKZ3Z, AC1MJ1T6, and GTPL4954.

5. Jojoba

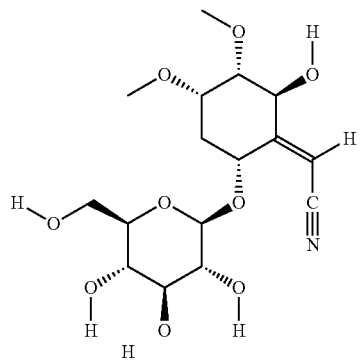

IUPAC Name
(2Z)-2-[(2S,3R,4S,6R)-2-hydroxy-3,4-dimethoxy-6-[(2R,3R,4S,5S,6R)-3,4,5-trihydroxy-6-(hydroxymethyl)oxan-2-yl]oxycyclohexylidene]acetonitrile cyclohexylidene)-, (2Z)-; Acetonitrile, (6-(beta-D-glucopyranosyloxy)-2hydroxy-3,4-dimethoxycyclohexylidene)-, (1Z,2-alpha,3-beta,4-beta,6-beta)-, Jojoba Meal Extract, and AC1O5NKM. Related compounds include Simmondsin:

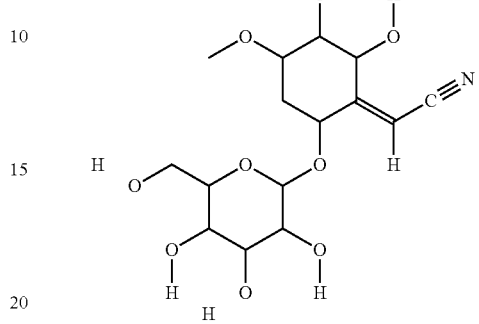

7. Curcumin

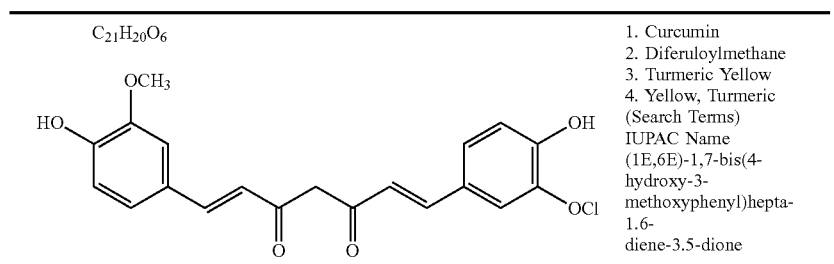

Jojoba oil (C16H25NO9) is a waxy liquid produced in the seed of the *Simmondsia chinensis* (Jojoba) plant, a shrub, which is native to southern Arizona, southern California, and northwestern Mexico.

Jojoba oil is used as an additive in many cosmetic products, especially those marketed from natural ingredients. In particular, such products containing jojoba are lotions and moisturizers, hair shampoos and conditioners. The pure oil itself may also be used on skin, hair, or cuticles. Jojoba oil can be hydrogenated, sulfonated, sulfurized. Extractives and their physically modified derivatives such as tinctures, concretes, absolutes, essential oils, oleoresins, terpenes, terpene-free fractions, distillates, residues, etc., obtained from *Simmondsia chinensis* N., Buxaceae can also be included in formulation embodiments of the invention.

Synonyms for jojoba also include Butanedioic acid; sulfo-, 4-(2-jojoba oil amidoethyl) esters, disodium salts; Partially Hydrogenated Jojoba Oil; Simmondsin; Jojoba oil; jojoba-wax; bean-oil; UNII-O51H15R39K; O51H15R39K; 2-(Cyanomethylene)-3-hydroxy-4,5-dimethoxycyclohexyl beta-D-glucoside, 51771-529; Acetonitrile, ((2S,3R,4S,6R)-6-(beta-D-glucopyranosyloxy)-2-hydroxy-3,4dimethoxy- Curcumin is a yellow-orange dye obtained from turmeric, the powdered root of *Curcuma longa*. It is used in the preparation of *curcuma* paper and the detection of boron. Curcumin appears to possess a spectrum of pharmacological properties, due primarily to its inhibitory effects on metabolic enzymes.

Curcumin is a phytopolylphenol pigment isolated from the plant *Curcuma longa*, commonly known as turmeric, with a variety of pharmacologic properties. Curcumin blocks the formation of reactive-oxygen species, possesses antiinflammatory properties as a result of inhibition of cyclooxygenases (COX) and other enzymes involved in inflammation; and disrupts cell signal transduction by various mechanisms including inhibition of protein kinase C. These effects may play a role in the agent's observed antineoplastic properties, which include inhibition of tumor cell proliferation and suppression of chemically induced carcinogenesis and tumor growth in animal models of cancer.

Curcumin is a natural component of the rhizome of turmeric (*Curcuma longa*) and one of the most powerful chemopreventive and anticancer agents. Its biological effects range from antioxidant, anti-inflammatory to inhibition of angiogenesis and is also shown to possess specific antitumoral activity. The molecular mechanism of its varied cellular effects has been studied in some details and it has been shown to have multiple targets and interacting macromolecules within the cell. Curcumin has been shown to possess anti-angiogenic properties and the angioinhibitory effects of curcumin manifest due to down regulation of proangiogenic genes such as VEGF and angiopoitin and a decrease in migration and invasion of endothelial cells. One of the important factors implicated in chemoresistance and induced chemosensitivity is NFkB and curcumin has been shown to down regulate NFkB and inhibit IKB kinase thereby suppressing proliferation and inducing apoptosis. Cell lines that are resistant to certain apoptotic inducers and radiation become susceptible to apoptosis when treated in conjunction with curcumin. Besides this it can also act as a chemopreventive agent in cancers of colon, stomach and skin by suppressing colonic aberrant crypt foci formation and DNA adduct formation.

Curcumin acts as a scavenger of oxygen species, such as hydroxyl radical, superoxide anion, and singlet oxygen and inhibit lipid peroxidation as well as peroxide-induced DNA damage. Curcumin mediates potent anti-inflammatory agent and anti-carcinogenic actions via modulating various signaling molecules. It suppresses a number of key elements in cellular signal transduction pathways pertinent to growth, differentiation, and malignant transformation; it was demonstrated in vitro that curcumin inhibits protein kinases, c-Jun/AP-1 activation, prostaglandin biosynthesis, and the activity and expression of the enzyme cyclooxygenase (COX)-2.

Synonyms include curcumin, 458-37-7, Diferuloylmethane, Natural yellow 3, Turmeric yellow, *Curcuma*, Turmeric, Kacha haldi, Gelbwurz, Indian saffron, Curcumin I, Souchet, Haidr, Halad, Haldar, Halud, Merita earth, Terra Merita, Yellow Ginger, Yellow Root, Safran d'Inde, Yo-Kin, *Curcuma* oil, Golden seal, Orange Root, Oils, *Curcuma*, C.I. Natural Yellow 3, Curcumine, Hydrastis, Indian turmeric, Yellow puccoon, Diferaloylmethane, Turmeric extract, Kurkumin [Czech], (1E,6E)-1,7-Bis(4hydroxy-3-methoxyphenyl)hepta-1,6-diene-3,5-dione, Tumeric yellow, Turmeric oil, Oil of turmeric, CI Natural Yellow 3, and Turmeric oleoresin.

8. Kinetin

Skoog et al. as a compound from autoclaved herring sperm DNA that had cell division-promoting activity. It was given the name kinetin because of its ability to induce cell division, provided that auxin was present in the medium.

Kinetin can react with UDP-D-glucose to produce kinetin-7-N-glucoside or kinetin-9-N-glucoside, with UDP as a byproduct. The reaction is catalyzed by UDP glycosyltransferase. Kinetin is a hormone derived from plants.

Kinetin is a member of the class of 6-aminopurines that is adenine carrying a (furan-2-ylmethyl) substituent at the exocyclic amino group. It is a member of furans and a member of 6-aminopurines.

Synonyms include Kinetin HCL; kinetin; 525-79-1; 6-Furfurylaminopurine; 6-Furfuryladenine; 6-(Furfurylamino)purine; N6-Furfuryladenine; N-Furfuryladenine; Cytokinin; N-(furan-2-ylmethyl)-9H-purin-6-amine; Cytex; N6-(Furfurylamino)purine; Kinetin (plant hormone); N-(furan-2-ylmethyl)-7H-purin-6-amine; Furfuryl(purin-6yl)amine; Adenine; N-furfuryl-1H-PURIN-6-AMINE; N-(2-FURANYLMETHYL)-; Kinetin (VAN); n(6)-furfuryladenine; Caswell No. 272D; 2-Furanmethanamine; N-1H-purin-6-yl-; N(sup 6)-Furfuryladenine; 9H-Purin-6-amine, N-(2-furanylmethyl)-; NSC 23119; UNIIP39Y9652YJ; N-(2-Furanylmethyl)-1H-purin-6-amine; N-(furan-2-ylmethyl)-1H-purin-6amine; N(sup 6)-(Furfurylamino)purine; HSDB 7429; EINECS 208-382-2; and EPA Pesticide Chemical Code 116801.

Compositions and compounds described in Chiu PC, Chan CC, Lin HM, Chiu HC: The clinical anti-aging effects of topical kinetin and niacinamide in Asians: a randomized, double-blind, placebo-controlled, split-face comparative trial. J Cosmet Dermatol. 2007 December; 6(4):243-9 can also be used in formulation embodiments of the invention, as well as compounds and compositions described in any one or more of U.S. Pat. Nos. 8,729,025; 8,404,660; and 8,222,260; and/or U.S. Patent Application Publication Nos. 2009/143279; 2008/139664.

9. Nicotinamide

| 8. KINETIN | |
|---|---|
| $C_{10}H_9N_5O$ | IUPAC Name<br>N-(furan-2-ylmethyl)-7H-purin-6-amine |

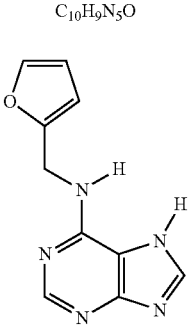 [SMILES: "C10H9N5O" ; c1coc(CNc2ncnc3nc[nH]c23)c1]

Kinetin, also known as 3H-Purin-6-amine, N-(2-furanylmethyl)-, 6-[(Furan2-ylmethyl)amino]-9H-purine, and 2-{[(9H-Purin-6-yl)amino]methyl}furan; 6-{[(Fur-2yl)methyl]amino}-9H-purine, is a type of cytokinin, a phytohormone, a plant growth regulator, a class of plant hormone that promotes cell division.

Kinetin is a furanyl adenine found in planta and fungi. It has plant growth regulation effects. Kinetin is a type of cytokinin, a class of plant hormone that promotes cell division. Kinetin was originally isolated by Miller and

| 9. NICOTINAMIDE | |
|---|---|
| $C_6H_6N_2O$<br>IUPAC<br>pyridine-3-carboxamide | 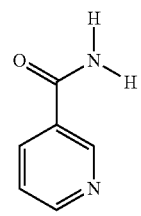 |

Nicotinamide, also known as niacinamide, is a form of vitamin B3 found in food and used as a dietary supplement and medication. As a supplement, it is used by mouth to prevent and treat pellagra (niacin deficiency). While nicotinic acid (niacin) may be used for this purpose, nicotinamide has the benefit of not causing skin flushing. As a cream, it is used to treat acne.

Niacinamide is the active form of vitamin B3 and a component of the coenzyme nicotinamide adenine dinucleotide (NAD). Niacinamide acts as a chemo- and radio-sensitizing agent by enhancing tumor blood flow, thereby reducing tumor hypoxia. This agent also inhibits poly(ADP-ribose) polymerases, enzymes involved in the rejoining of DNA strand breaks induced by radiation or chemotherapy.

Niacinamide or vitamin B3 is an important compound functioning as a component of the coenzyme NAD. Its primary significance is in the prevention and/or cure of blacktongue and pellagra. Most animals cannot manufacture this compound in amounts sufficient to prevent nutritional deficiency and it therefore must be supplemented through dietary intake. Niacinamide is used to increase the effect of radiation therapy on tumor cells. Niacin (nicotinic acid) and niacinamide, while both labeled as vitamin B3 also have different applications. Niacinamide is useful in arthritis and early-onset type I diabetes while niacin is an effective reducer of high cholesterol levels. Related compounds include Isonicotinamide, Nicotinamide riboside, and the following:

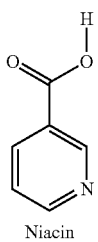
Niacin

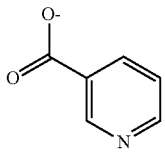
Pyrazinamide

Nicotinate

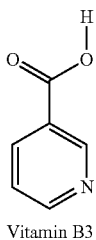
Vitamin B3

Synonyms include nicotinamide, niacinamide, 98-92-0,3-Pyridinecarboxamide, Nicotinic acid amide, pyridine-3-carboxamide, vitamin PP, Papulex, Aminicotin, Amixicotyn, Nicobion, Nicotylamide, Nikotinamid, Savacotyl, Benicot, Dipegyl, Endobion, Hansamid, Pelmine, Nicotinic amide, Delonin amide, Pelonin amide, Vi-Nicotyl, Austrovit PP, Inovitan PP, Vitamin B, Nicosylamide, Nicotilamide, Nicotililamido, Amnicotin, Niacevit, Nicamina, Nicamindon, Nicofort, Nicomidol, Nicotamide, Nicovitina, Nicovitol, Nicozymin, Niocinamide, Niozymin, Niamide, Nicasir, Nicogen, Nicota, Nicotol, Nicovit, Niko-tamin, and 3-Carbamoylpyridine, Nicotine a. Any one or more of these can be included in the formulations according to embodiments of the invention, including and composition or compound described in U.S. Pat. No. 8,288,434.

Particular Embodiments

Embodiments of this disclosure are meant to include the following chemicals directed in use as described and including palmitic molecules and the capsaicinoids, capsaicin analogs and derivatives outlined below:

Carbamate:

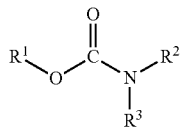

A carbamate is an organic compound derived from carbamic acid (NH2COOH). A carbamate group, carbamate ester (e.g., ethyl carbamate), and carbamic acids are functional groups that are inter-related structurally. Carbamate esters are also called urethanes.

Carboxylic Acids

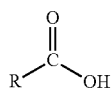

A carboxylate is the conjugate base of a carboxylic acid. Carboxylate esters have the general formula RCOOR'. R and R' are organic groups; R'≠H. A carboxylic acid is an organic compound that contains a carboxyl group. The general formula of a carboxylic acid is R—COOH, with R referring to the rest of the molecule.

Capsaicin:

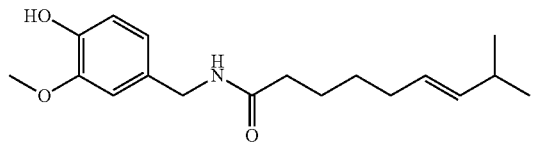 [SMILES: COc1cc(CNC(=O)CCCC/C=C/C(C)C)ccc1O]

Capsaicin is used as an analgesic in topical ointments, salves, creams and dermal patches to relieve pain, typically in concentrations between 0.025% and 0.1%. Capsaicin achieves its pain-relieving effect by reversibly depleting sensory nerve endings of Substance P, an undecapeptide released from sensory nerves and by reducing the density of epidermal nerve fibers, in a reversible manner. Related compounds include the following:

| RELATED COMPOUNDS | |
|---|---|
| N-((4-(2-Aminoethoxy)-3-methoxyphenyl)methyl)-9-octadecenamide | 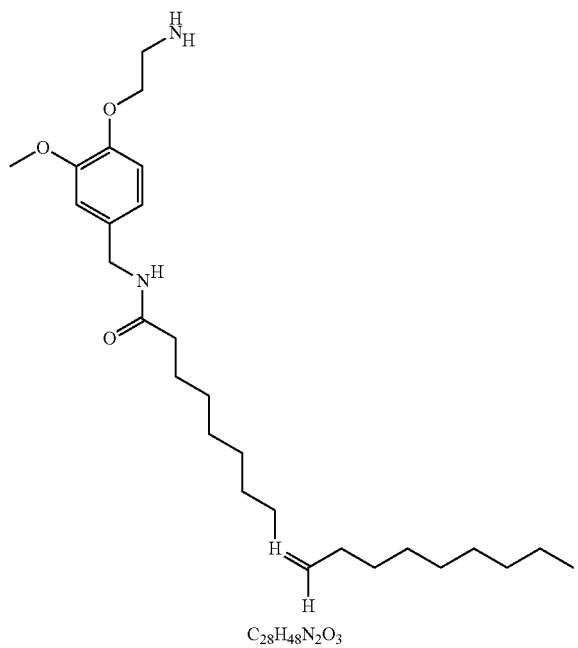<br>$C_{28}H_{48}N_2O_3$ |
| Sodium nonivamide acetate;<br>Acetic acid, (2-methoxy-4-(((1-oxononyl)amino)methyl)phenoxy)<br>monosodium salt | 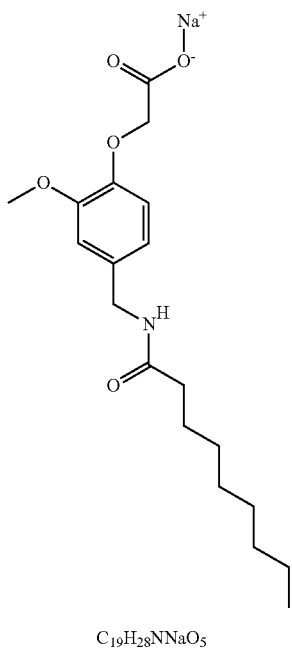<br>$C_{19}H_{28}NNaO_5$ |

Capsaicinoids:

Gapsaicinoids and their close analogs capsinoids, are comprised of a relatively polar vanillyl head group, a long hydrophobic chain, and an amide or ester linkage for capsaicinoids and capsinoids respectively. While all three components have been identified as critical for the associated biological and pharmacological activities, chemical synthesis of analogs of both families have been extensively carried out on the head group and/or the hydrophobic chain (for some of the recent examples, see: Moriello, A. S. et al. J. Med. Chem., Just Accepted Manuscript, Publication Date (Web): 3 Sep. 2018; Serafini, M. et al. J. Med. Chem., 2018, 61, 4436-4455; Ramsaywack, S. et al. Canadian Journal of Chemistry, Manuscript ID: cjc-2018-0193.R1, date submitted: 2 Jul. 2018; Aiello, F. et al. ACS Chem. Neurosci. 2016, 7, 737-748; Barbero, G. et al. J. Agric. Food Chem. 2010, 58, 3342-3349; Appendino, G. et al. J. Med. Chem. 2002, 45, 3739-3745). Based on a general pharmacophore model of capsaicinoids and capsinoids, large efforts have also been devoted to the design and synthesis of antagonists and agonists targeting TRPV-1 for pain relief, resulting in small molecules that bear little resemblance to the natural ligands such as capsaicin and capsicin (for selected examples, please see: Mostinski, Y. et al. ACS Chem. Neurosci. 2017, 8, 1688-1696; Parsons, W. H. et al. J. Med. Chem. 2015, 58, 3859-3874; Blum, C. A. et al. J. Med. Chem. 2010, 53, 3330-3348; Ognyanov, V. I. et al. J. Med. Chem. 2006, 49, 3719-3742).

Topical application of capsaicinoids causes intense burning over the treatment area. Capsaicinoids may include the following:

Palmitates:

Palmitates are the salts and esters of palmitic acid.

Palmitic Acid (Hexadecanoic Acid):

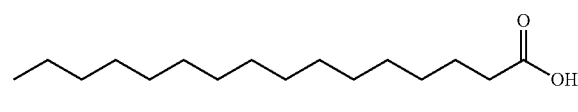

Palmitic acid is the first cellular fatty acid produced during fatty acid synthesis and is the precursor to longer fatty acids.

This embodiment includes di- and tri-palmitic acid, Glycerin di- and tripalmiate, palmitin and their palmitic esters.

| Capsaicinoids | |
|---|---|
| Capsaicin | 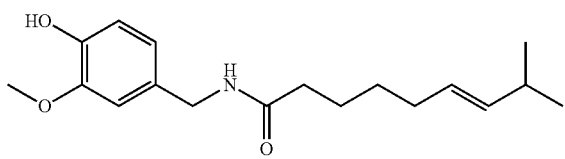 [SMILES: COc1cc(CNC(=O)CCCC/C=C/C(C)C)ccc1O] |
| Dihydrocapsaicin | 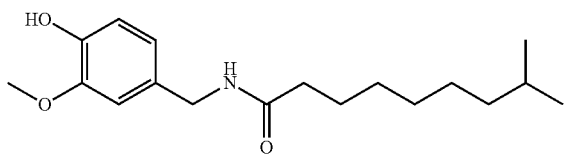 [SMILES: COc1cc(CNC(=O)CCCCCCC(C)C)ccc1O] |
| Nordihydrocapsaicin | 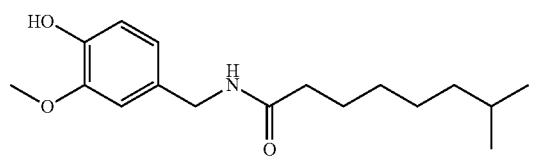 [SMILES: COc1cc(CNC(=O)CCCCCC(C)C)ccc1O] |
| Homocapsaicin | 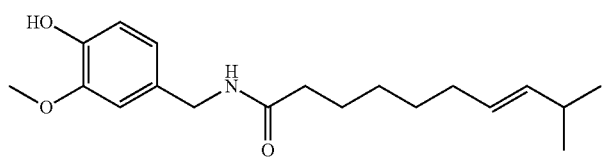 [SMILES: COc1cc(CNC(=O)CCCCC/C=C/C(C)C)ccc1O] |
| Homodihydrocapsaicin | 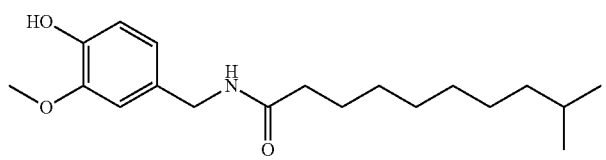 [SMILES: COc1cc(CNC(=O)CCCCCCCC(C)C)ccc1O] |
| Nonivamide (synthetic) | 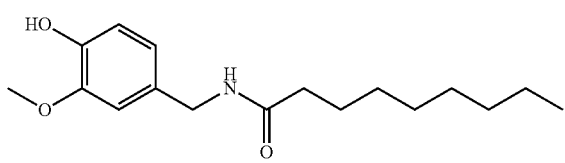 [SMILES: CCCCCCCCC(=O)NCc1ccc(O)c(OC)c1] |

Includes capsaicinol, capsaicin diacetate, capsaicin dipalmate and capsazepine.

Capsiate:

Capsiate, with an ester linkage between the vanilloid head group and the fatty acid tail, and an overall more hydrophobic molecule, does not cause such burning sensation. An ester prodrug formed between the capsaicin phenolic hydroxyl and a long chain fatty acid causes essentially no irritation when applied topically, presumably the increased hydrophobicity and facilitated dermal uptake of the resulting molecule play a significant role (Singh, C. U. et al. U.S. Pat. No. 7,943,666). Use of ester for the protection of alcohol has hydrolytic or instability liability since esters are prone to enzymatic hydrolysis. The stability of an ester depends on the structure of both the acid and the hydroxyl partners. A phenolic ester (ester formed between a carboxylic acid and a phenol) is particularly labile due to phenol being a better leaving group compared to an aliphatic alcohol (Blay, G. et al. Synthesis 1989, 438-439). Besides esters, prodrugs of capsaicinoids have also been generated between the phenolic hydroxyl group and another molecule of hydroxyl containing compound using a carbonate ester linkage (Jamieson, G. C. et al. U.S. Pat. No. 7,632,519). Carbonate and ether linkages have also been utilized for a transient phenolic alcohol protection using photolytically cleavable molecular partners (Katritzky, A. R. et al. J. Org. Chem. 2003, 68, 9100-9104).

The chemical stability of a carbamate is generally considered to be somewhere between an ester and an amide, and they can be substrates for both esterases and amidases (for a recent review on prodrug approach in drug discovery, see: Rautio, J. et al. Nat. Rev. Drug Discov. 2018, 17, 559-587). Examples of simple aliphatic amines conjugated to a capsaicin with a carbamate linkage, thereby functioning as a protecting group for the analgesics, exist in the literature. Here, in embodiments, the use of amines with one extra functional group such as a carboxyl or a hydroxyl can be used as a handle for attachment of a second molecule, either inert for additional hydrophobicity or from using a molecule with biological and pharmacological activity (such as a known drug) for possible modulation of the overall therapeutic profile. In embodiments, amino containing heterocycles or heteroaryls with varied structural complexity can be used as capsaicin prodrug partners for carbamate linkage stability modulation and tuning (see, e.g., FIG. 1).

Fatty Acid Assessment of Capsaicin Palmitate

Pharmaceutical compounds may be palmitated. This is a preferred embodiment used to reduce or eliminate capsaicin pungency. Capsaicin is a highly selective agonist for TRPV1. TRPV1 is a ligand-gated, non-selective cation channel preferentially expressed on small-diameter sensory neurons, especially C-fibers that specialize in the detection of painful or noxious sensations. TRPV1 responds to noxious stimuli including capsaicin, heat, and extracellular acidification, and will integrate simultaneous exposures to these stimuli.

Reduction of the inherent pungency of capsaicin, its analogs and other TRPV1 agonists through modification of the chemical structure of the parent molecule is disclosed by the present invention. Here, it has been surprisingly discovered that in order to avoid the burning properties of capsaicin on the skin, by design, a pro-drug such as capsaicin palmitate can be made where a linker or helper molecule such as a fatty acid, can be released leaving the capsaicin molecule or its structural derivative, that can be independently delivered to the TRPV1-associated neuron, and/or after the molecule has reached its site of action. Therefore, the chemical-release kinetics of a parent drug may impart two important properties: (a) reduced and/or delayed pungency and (b) prolonged and slow release for extended duration of pharmacological activity.

The capsaicin, capsaicinoids or other TRPV1 agonist compounds can be chemically modified to control the rate at which capsaicin, capsaicinoid, or other TRPV1 agonist (from here, capsaicin) is bioavailable through enzymatic and/or hydrolytic conversions of side chains. In the case of CP, an ester or other hydrolyzable linker group may be covalently bonded to the phenol position of capsaicin such that upon administration, enzymes and/or water may induce hydrolysis of the linkage to liberate the capsaicin molecule where the hydrolyzable group acts to sterically hinder the pungent moiety of the capsaicin molecule.

Fatty acids and their associated derivatives are the primary components of lipids. The length and degree of saturation of the hydrocarbon chain is highly variable between each fatty acid, and dictates the associated physical properties (e.g., melting point and fluidity). Moreover, the hydrocarbon chains of fatty acids are responsible for the hydrophobic properties (insoluble in water) exhibited by lipids. Fatty acids, like capsaicin, are comprised of hydrocarbon chains (saturated and unsaturated, respectively). However, while fatty acids terminate with carboxylic acid groups and capsaicin terminates with a 4-hydroxy-3-methoxyphenyl ring, these are both hydrophilic structures. These aliphatic structures are similar in some areas and different in others, thereby rendering the molecules chemically compatible.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compounds and/or compositions disclosed herein or with any other compounds and/or compositions. Likewise, any of the disclosed compounds and/or compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range, to the tenth of the unit disclosed, is also specifically disclosed. Any smaller range within the ranges disclosed or that can be derived from other endpoints disclosed are also specifically disclosed themselves. The upper and lower limits of disclosed ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A prodrug of formula (I), (II) or (III):

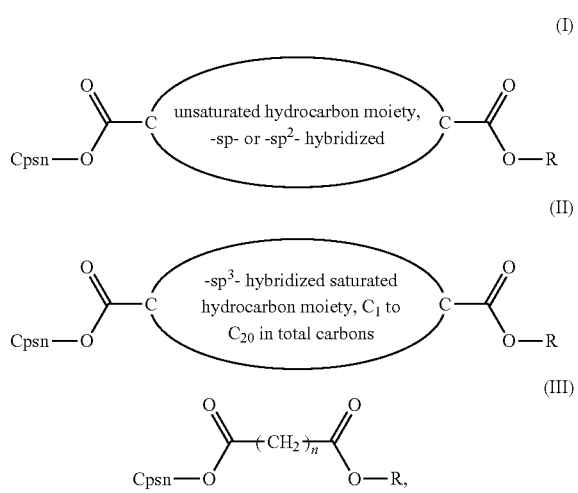

wherein:
Cpsn represents a capsaicinoid which is joined at a free phenolic hydroxyl group via an ester-containing linkage of formula (I), (II) or (III);
R in formula (I), (II) and (III) is a $C_{1-20}$ branched, cyclized, saturated or unsaturated hydrocarbon, a molecule with analgesic properties, or a molecule with pharmacological properties; and
the unsaturated hydrocarbon moiety in formula (I) is a non-cyclic moiety having two carbon atoms, or
the unsaturated hydrocarbon moiety in formula (I) is a benzene moiety that is optionally substituted with up to four substituents selected from the group consisting of a straight, branched or cyclic $C_{1-6}$ hydrocarbon, a halogen, a hydroxyl, an alkoxyl, a nitrogen-containing substituent, and any combination thereof, such that two adjacent substituents may be joined to form a fused heterocyclic ring;
the saturated hydrocarbon moiety in formula (II) is a branched or cyclic C1-C20 hydrocarbon moiety; and
n is 6 to 20.

2. The prodrug of claim 1, which is a prodrug of formula (I).

3. The prodrug of claim 1, which is a prodrug of formula (II).

4. The prodrug of claim 1, which is a prodrug of formula (III).

5. The prodrug of claim 1, wherein R is a $C_{1-20}$ branched, cyclized, saturated or unsaturated hydrocarbon.

6. The prodrug of claim 1, wherein R is a molecule with analgesic properties, or a molecule with pharmacological properties.

7. The prodrug of claim 6, wherein R is Cpsn.

8. The prodrug of claim 2, wherein the unsaturated hydrocarbon moiety in formula (I) is the non-cyclic moiety having two carbon atoms.

9. The prodrug of claim 8, wherein the unsaturated hydrocarbon moiety having two carbon atoms derives from an α,β-unsaturated di-carboxylic acid comprising carbon atoms.

10. The prodrug of claim 2, wherein the unsaturated hydrocarbon moiety in formula (I) is the benzene moiety that is optionally substituted with up to four substituents selected from the group consisting of a straight, branched or cyclic $C_{1-6}$ hydrocarbon, a halogen, a hydroxyl, an alkoxyl, a nitrogen-containing substituent, and any combination thereof, wherein two adjacent substituents may be joined to form a fused heterocyclic ring.

11. The prodrug of claim 10, wherein the benzene moiety is optionally substituted with up to four substituents selected from the group consisting of a cyclic $C_{3-6}$ hydrocarbon, a halogen, an alkoxy, and any combination thereof, wherein two adjacent alkoxy substituents may be joined to form a fused heterocyclic ring.

12. The prodrug of claim 11, wherein the benzene moiety is a structure of formula:

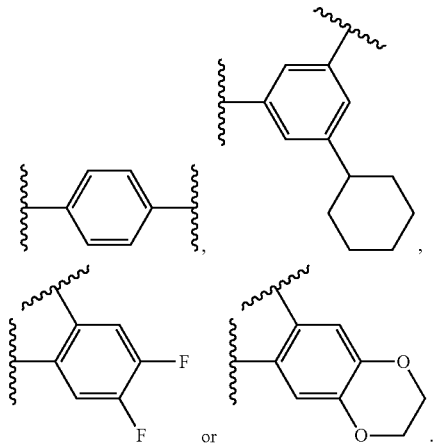

13. The prodrug of claim 3, wherein the saturated hydrocarbon moiety in formula (II) is a branched $C_1$-$C_{20}$ hydrocarbon moiety.

14. The prodrug of claim 3, wherein the saturated hydrocarbon moiety in formula (II) is a cyclic $C_1$-$C_{20}$ hydrocarbon moiety.

15. A composition, comprising: the prodrug of claim 1, and at least one of water, an oil, a surfactant, an emulsifier, a stabilizer, a chelator, a preservative, and a pH-adjusting agent.

* * * * *

UNITED STATES PATENT AND TRADEMARK OFFICE
CERTIFICATE OF CORRECTION

| | | |
|---|---|---|
| PATENT NO. | : 12,358,868 B2 | Page 1 of 1 |
| APPLICATION NO. | : 18/454685 | |
| DATED | : July 15, 2025 | |
| INVENTOR(S) | : Richard Daniel Carliss et al. | |

It is certified that error appears in the above-identified patent and that said Letters Patent is hereby corrected as shown below:

In the Claims

<u>Column 34, Claim 9, Line 14:</u>
"acid comprising carbon" should read: --acid comprising 4 carbon--.

Signed and Sealed this
Twenty-eighth Day of October, 2025

John A. Squires
*Director of the United States Patent and Trademark Office*